United States Patent [19]
Abrams et al.

[11] Patent Number: 5,341,818
[45] Date of Patent: Aug. 30, 1994

[54] GUIDEWIRE WITH SUPERELASTIC DISTAL PORTION

[75] Inventors: Robert M. Abrams, Carlsbad; Randy S. Chan, San Jose; Janet W. Burpee, Santa Clara; Clifford Teoh, Daly City, all of Calif.

[73] Assignee: Advanced Cardiovascular Systems, Inc., Santa Clara, Calif.

[21] Appl. No.: 994,679

[22] Filed: Dec. 22, 1992

[51] Int. Cl.5 ............................... A61B 5/00
[52] U.S. Cl. ........................................ 128/772
[58] Field of Search ............... 128/657, 772; 604/95, 604/280–283

[56] References Cited

U.S. PATENT DOCUMENTS

| | | |
|---|---|---|
| 4,665,906 | 5/1987 | Jervis . |
| 4,827,941 | 5/1989 | Taylor et al. .................. 128/772 |
| 4,875,489 | 10/1989 | Messner et al. ............... 128/657 |
| 4,881,981 | 11/1989 | Thomas et al. . |
| 4,925,445 | 5/1990 | Sakamoto et al. .............. 604/95 |
| 4,935,068 | 6/1990 | Duerig . |
| 4,984,581 | 1/1991 | Stice ............................. 128/772 |
| 5,069,226 | 12/1991 | Yamauchi et al. ............. 128/772 |
| 5,120,308 | 6/1992 | Hess .............................. 604/95 |
| 5,143,085 | 9/1992 | Wilson .......................... 128/772 |
| 5,188,621 | 2/1993 | Samson .......................... 128/657 |

Primary Examiner—Max Hindenburg
Attorney, Agent, or Firm—Crosby, Heafey, Roach & May

[57] ABSTRACT

An improved guidewire for advancing a catheter within a body lumen which has a high strength proximal portion, a distal portion formed of superelastic alloy and a connector formed of superelastic alloy to provide a torque transmitting coupling between the distal end of the proximal portion and the proximal end of the distal portion. The superelastic alloy elements are preferably cold worked and then heat treated at a temperature well above the austenite-to-martensite transformation temperature, while being subjected to longitudinal stresses equal to about 5 to about 50% of the room temperature yield stress to impart to the metal a straight "memory". The guiding member using such improved material exhibits a stress induced austenite-to-martensite phase transformation at an exceptionally high constant yield strength of at least 70 ksi for solid members and at least 50 ksi for tubular members with a broad recoverable strain of at least about 4% during the phase transformation.

24 Claims, 1 Drawing Sheet

GUIDEWIRE WITH SUPERELASTIC DISTAL PORTION

BACKGROUND OF THE INVENTION

This invention relates to the field of medical devices, and more particularly to guiding means such as a guidewire for advancing a catheter within a body lumen in a procedure such as percutaneous transluminal coronary angioplasty (PTCA).

In a typical PTCA procedure a guiding catheter having a preformed distal tip is percutaneously introduced into the cardiovascular system of a patient in a conventional Seldinger technique and advanced therein until the distal tip of the guiding catheter is seated in the ostium of a desired coronary artery. A guidewire is positioned within an inner lumen of a dilatation catheter and then both are advanced through the guiding catheter to the distal end thereof. The guidewire is first advanced out of the distal end of the guiding catheter into the patient's coronary vasculature until the distal end of the guidewire crosses a lesion to be dilated, then the dilatation catheter having an inflatable balloon on the distal portion thereof is advanced into the patient's coronary anatomy over the previously introduced guidewire until the balloon of the dilatation catheter is properly positioned across the lesion. Once in position across the lesion, the balloon is inflated to a predetermined size with radiopaque liquid at relatively high pressures (e.g. greater than 4 atmospheres) to compress the arteriosclerotic plaque of the lesion against the inside of the artery wall and to otherwise expand the inner lumen of the artery. The balloon is then deflated so that blood flow is resumed through the dilated artery and the dilatation catheter can be removed therefrom.

Conventional guidewires for angioplasty and other vascular procedures usually comprise an elongated core member with one or more tapered sections near the distal end thereof and a flexible body such as a helical coil disposed about the distal portion of the core member. A shapable member, which may be the distal extremity of the core member or a separate shaping ribbon which is secured to the distal extremity of the core member extends through the flexible body and is secured to a rounded plug at the distal end of the flexible body. Torquing means are provided on the proximal end of the core member to rotate, and thereby steer, the guidewire while it is being advanced through a patient's vascular system.

Further details of dilatation catheters, guidewires, and devices associated therewith for angioplasty procedures can be found in U.S. Pat. No. 4,323,071 (Simpson-Robert); U.S. Pat. No. 4,439,185 (Lundquist); U.S. Pat. No. 4,516,972 (Samson); U.S. Pat. No. 4,538,622 (Samson et al.); U.S. Pat. No. 4,554,929 (Samson et al.); U.S. Pat. No. 4,616,652 (Simpson); and U.S. Pat. No. 4,638,805 (Powell) which are hereby incorporated herein in their entirety by reference thereto.

Steerable dilatation catheters with fixed, built-in guiding members, such as described in U.S. Pat. No. 4,582,181 (now Re 33,166) are frequently used because they have lower deflated profiles than conventional over-the-wire dilatation catheters and a lower profile allows the catheter to cross tighter lesions and to be advanced much deeper into a patient's coronary anatomy.

A major requirement for guidewires and other guiding members, whether they be solid wire or tubular members, is that they have sufficient column strength to be pushed through a patient's vascular system or other body lumen without kinking. However, they must also be flexible enough to avoid damaging the blood vessel or other body lumen through which they are advanced. Efforts have been made to improve both the strength and flexibility of guidewires to make them more suitable for their intended uses, but these two properties are for the most part diametrically opposed to one another in that an increase in one usually involves a decrease in the other.

The prior art makes reference to the use of alloys such as Nitinol (Ni—Ti alloy) which have shape memory and/or superelastic characteristics in medical devices which are designed to be inserted into a patient's body. The shape memory characteristics allow the devices to be deformed to facilitate their insertion into a body lumen or cavity and then be heated within the body so that the device returns to its original shape. Superelastic characteristics on the other hand generally allow the metal to be deformed and restrained in the deformed condition to facilitate the insertion of the medical device containing the metal into a patient's body, with such deformation causing the phase transformation. Once within the body lumen the restraint on the superelastic member can be removed, thereby reducing the stress therein so that the superelastic member can return to its original undeformed shape by the transformation back to the original phase.

Alloys having shape memory/superelastic characteristics generally have at least two phases, a martensite phase, which has a relatively low tensile strength and which is stable at relatively low temperatures, and an austenite phase, which has a relatively high tensile strength and which is stable at temperatures higher than the martensite phase.

Shape memory characteristics are imparted to the alloy by heating the metal at a temperature above which the transformation from the martensite phase to the austenite phase is complete, i.e. a temperature above which the austenite phase is stable. The shape of the metal during this heat treatment is the shape "remembered". The heat treated metal is cooled to a temperature at which the martensite phase is stable, causing the austenite phase to transform to the martensite phase. The metal in the martensite phase is then plastically deformed, e.g. to facilitate the entry thereof into a patient's body. Subsequent heating of the deformed martensite phase to a temperature above the martensite to austenite transformation temperature causes the deformed martensite phase transform to the austenite phase and during this phase transformation the metal reverts back to its original shape.

The prior methods of using the shape memory characteristics of these alloys in medical devices intended to be placed within a patient's body presented operational difficulties. For example, with shape memory alloys having a stable martensite temperature below body temperature, it was frequently difficult to maintain the temperature of the medical device containing such an alloy sufficiently below body temperature to prevent the transformation of the martensite phase to the austenite phase when the device was being inserted into a patient's body. With intravascular devices formed of shape memory alloys having martensite-to-austenite transformation temperatures well above body temperature, the devices could be introduced into a patient's body with little or no problem, but they had to be heated to the martensite-to-austenite transformation temperature which was frequently high enough to cause tissue damage and very high levels of pain.

When stress is applied to a specimen of a metal such as Nitinol exhibiting superelastic characteristics at a temperature at or above which the transformation of martensite phase to the austenite phase is complete, the specimen deforms elastically until it reaches a particular stress level where the alloy then undergoes a stress-induced phase transformation from the austenite phase to the martensite phase. As the phase transformation proceeds, the alloy undergoes significant increases in strain but with little or no corresponding increases in stress. The strain increases while the stress remains essentially constant until the transformation of the austenite phase to the martensite phase is complete. Thereafter, further increase in stress are necessary to cause further deformation. The martensitic metal first yields elastically upon the application of additional stress and then plastically with permanent residual deformation.

If the load on the specimen is removed before any permanent deformation has occurred, the martensitic specimen will elastically recover and transform back to the austenite phase. The reduction in stress first causes a decrease in strain. As stress reduction reaches the level at which the martensite phase transforms back into the austenite phase, the stress level in the specimen will remain essentially constant (but substantially less than the constant stress level at which the austenite transforms to the martensite) until the transformation back to the austenite phase is complete, i.e. there is significant recovery in strain with only negligible corresponding stress reduction. After the transformation back to austenite is complete, further stress reduction results in elastic strain reduction. This ability to incur significant strain at relatively constant stress upon the application of a load and to recover from the deformation upon the removal of the load is commonly referred to as superelasticity or pseudoelasticity.

The prior art makes reference to the use of metal alloys having superelastic characteristics in medical devices which are intended to be inserted or otherwise used within a patient's body. See for example, U.S. Pat. No. 4,665,905 (Jervis) and U.S. Pat. No. 4,925,445 (Sakamoto et al.).

The Sakamoto et al. patent discloses the use of a nickel-titanium superelastic alloy in an intravascular guidewire which could be processed to develop relatively high yield strength levels. However, at the relatively high yield stress levels which cause the austenite-to-martensite phase transformation characteristic of the material, it did not have a very extensive stress-induced strain range in which the austenite transforms to martensite at relative constant stress. As a result, frequently as the guidewire was being advanced through a patient's tortuous vascular system, it would be stressed beyond the superelastic region, i.e. develop a permanent set or even kink which can result in tissue damage. This permanent deformation would generally require the removal of the guidewire and the replacement thereof with another.

Products of the Jervis patent on the other hand had extensive strain ranges, i.e. 2 to 8% strain, but the relatively constant stress level at which the austenite transformed to martensite was very low, e.g. 50 ksi.

In copending application Ser. No. 07/629,381, filed Dec. 18, 1990 entitled Superelastic Guiding Member, guide wires or guiding members are described which have at least a solid or tubular portion thereof exhibiting superelastic characteristics including an extended strain region over a very high, relatively constant high stress level which effects the austenite transformation to martensite. While the properties of the guidewire formed of the superelastic material were very advantageous, it was found that the guidewires and guiding members formed of materials having superelastic characteristics did not have optimum push and torque characteristics.

SUMMARY OF THE INVENTION

The present invention is directed to improve guidewires or guiding members, wherein the distal portion is provided with superelastic characteristics resulting from the stress-induced transformation of austenite to martensite and wherein the proximal portion is provided with high strength elastic materials.

The guidewire or guiding member of the invention has a high strength proximal section with a high strength distal section with superelastic properties and a connector element between the proximal and distal sections which has superelastic properties to provide a smooth transition between the proximal and the distal sections. In a presently preferred embodiment the guidewire or guiding member has a solid core distal section formed of superelastic materials such as NiTi type alloys and the connector is a hollow tubular shaped member which has a inner passageway adapted to receive the proximal end of the solid core distal section.

The superelastic distal core member and the hollow connector of the invention exhibit stress-induced phase transformation at body temperature (about 37° C.) at a stress level well above about 50 ksi, preferably above 70 ksi and in many cases above about 90 ksi. The complete stress-induced transformation of the austenite phase to the martensite phase causes a strain in the specimen of at least about 4%, preferably over 5%. The region of phase transformation resulting from stress preferably begins when the specimen has been strained about 2 to 3% at the onset of the phase change from austenite to martensite and extends to about 7 to about 9% strain at the completion of the phase change. The stress and strain referred to herein is measured by tensile testing. The stress-strain relationship determined by applying a bending moment to a cantilevered specimen is slightly different from the relationship determined by tensile testing because the stresses which occur in the specimen during bending are not as uniform as they are in tensile testing. There is considerably less change in stress during the phase transformation than either before or after the stress-induced transformation. The stress level is relatively constant within the transformation period.

The portions of the guiding member having superelastic properties is preferably formed from an alloy consisting essentially of about 30 to about 52% titanium and the balance nickel and up to 10% of one or more additional alloying elements. Such other alloying elements may be selected from the group consisting of up to 3% each of iron, cobalt, platinum, palladium and chromium and up to about 10% copper and vanadium. As used herein all references to percent composition are atomic percent unless otherwise noted.

To form the elongated superelastic portion of the guiding member, elongated solid rod or tubular stock of the preferred alloy material is first cold worked, preferably by drawing, to effect a size reduction of about 30% to about 70% in the transverse cross section thereof.

The cold worked material may then be given a memory imparting heat treatment at a temperature of about 350° to about 600° C. for about 0.5 to about 60 minutes, while maintaining a longitudinal stress on the elongated portion equal to about 5% to about 50%, preferably about 10% to about 30%, of the yield stress of the material (as measured at room temperature). This thermomechanical processing imparts a straight "memory" to the superelastic portion and provides a relatively uniform residual stress in the material. Another method involves mechanically straightening the wire after the cold work and then heat treating the wire at temperatures between about 300° and about 450° C., preferably about 330° to about 400° C. The latter treatment provides substantially higher tensile properties. The cold worked and heat treated alloy material has an austenite finish transformation temperature less than body temperature and generally about −10° C. to about 30° C. For more consistent final properties, it is preferred to fully anneal the solid rod or tubular stock prior to cold work so that the material will always have the same metallurgical structure at the start of the cold working and so that it will have adequate ductility for subsequent cold working. It will be appreciated by those skilled in the art that means of cold working the metal other than drawing, such as rolling or swaging, can be employed. The constant yield stress levels for tubular products have been found to be slightly lower than the levels for solid products. For example, superelastic wire material of the invention will have a constant stress level usually above about 70 ksi, preferably above about 90 ksi, whereas, superelastic tubing material will have a constant stress level of above 50 ksi, preferable above about 70 ksi. The ultimate tensile strength of both forms of the material is well above 200 ksi with an ultimate elongation at failure of about 15%.

The elongated superelastic members of the invention exhibit stress-induced austenite-to-martensite phase transformation over a broad region of strain at a very high, relatively constant stress levels. As a result a guiding member having a distal portion formed of this material is very flexible, it can be advanced through very tortuous passageways such as a patient's coronary vasculature with little risk that the superelastic portion of the guiding member will develop a permanent set and at the same time it will effectively transmit the torque applied thereto without causing the guiding member to whip. The high strength proximal portion of the guidewire or guiding member provides excellent pushability and torquability to the guidewire or guiding member.

These and other advantages of the invention will become more apparent from the following detailed description thereof when taken in conjunction with the following exemplary drawings.

DETAILED DESCRIPTION OF THE INVENTION

Figure 1:
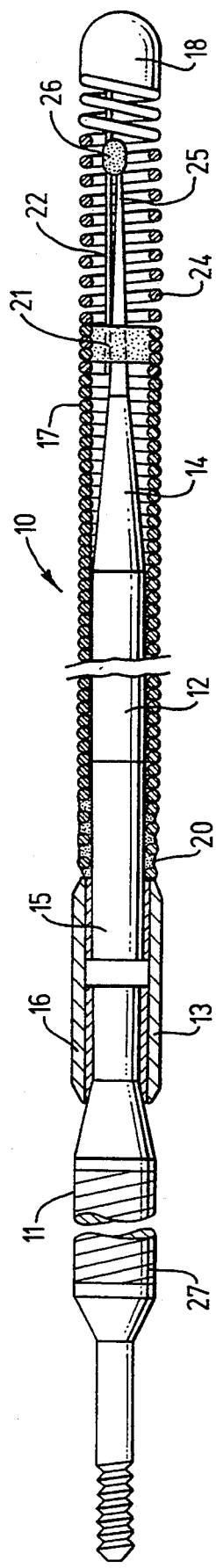
FIG. 1 is an elevational view of a guidewire which embodies features of the invention.

FIG. 1 illustrates a guidewire 10 embodying features of the invention that is adapted to be inserted into a patient's body lumen, such as an artery. The guidewire 10 comprises an elongated, relatively high strength proximal portion 11, a relatively short distal portion 12 which is formed substantially of superelastic alloy material and a connector element 13 which is formed substantially of superelastic alloy material and which connects the proximal end of the distal portion 12 to the distal end of the proximal portion 11 into a torque transmitting relationship. The distal portion 12 has at least one tapered section 14 which becomes smaller in the distal direction. The connector element 13 is a hollow tubular shaped element having an inner lumen extending therein which is adapted to receive the proximal end 15 of the distal portion 12 and the distal end 16 of the proximal portion 11. The ends 15 and 16 may be press fit into the connector element or they may be secured therein by crimping or swaging the connector or by means such as a suitable adhesive or by welding, brazing or soldering.

A helical coil 17 is disposed about the distal portion 12 and has a rounded plug 18 on the distal end thereof. The coil 17 is secured to the distal portion 12 at proximal location 20 and at intermediate location 21 by a suitable solder. A shaping ribbon 22 is secured by its proximal end to the distal portion 12 at the same location 21 by the solder and by the distal end thereof to the rounded plug 18 which is usually formed by soldering or welding the distal end of the coil 17 to the distal tip of the shaping ribbon 22. Preferably, the most distal section 24 of the helical coil 17 is made of radiopaque metal such as platinum or platinum-nickel alloys to facilitate the observation thereof while it is disposed within a patient's body. The most distal section 24 should be stretched about 10 to about 30%.

The most distal part 25 of the distal portion 12 is flattened into a rectangular section and preferably provided with a rounded tip 26, e.g. solder to prevent the passage of the most distal part through the spacing between the stretched distal section 24 of the helical coil 17.

The exposed portion of the elongated proximal portion 11 should be provided with a coating 27 of lubricous material such as polytetrafluoroethylene (sold under the trademark Teflon by du Pont, de Nemours & Co.) or other suitable lubricous coatings such as the polysiloxane coatings disclosed in co-pending application Ser. No. 559,373, filed Jul. 24, 1990 which is hereby incorporated by reference.

The elongated proximal portion 11 of the guidewire 10 is generally about 130 to about 140 cm in length with an outer diameter of about 0.006 to 0.018 inch for coronary use. Larger diameter guidewires may be employed in peripheral arteries and other body lumens. The lengths of the smaller diameter and tapered sections can range from about 2 to about 20 cm, depending upon the stiffness or flexibility desired in the final product. The helical coil 17 is about 20 to about 45 cm in length, has an outer diameter about the same size as the diameter of the elongated proximal portion 11, and is made from wire about 0.002 to 0.003 inch in diameter. The shaping ribbon 22 and the flattened distal section 26 of distal portion 12 have rectangular transverse cross-sections which usually have dimensions of about 0.001 by 0.003 inch.

The superelastic members of the invention, i.e. the distal portion 12 and the connector 13, is preferably made of an alloy material consisting essentially of about 30 to about 52% titanium and the balance nickel and up to 10% of one or more other alloying elements. The other alloying elements may be selected from the group consisting of iron, cobalt, vanadium, platinum, palladium and copper. The alloy can contain up to about 10% copper and vanadium and up to 3% of the other alloying elements. The addition of nickel above the equiatomic amounts with titanium and the other identified alloying elements increase the stress levels at which the stress-induced austenite-to-martensite transformation occurs and ensure that the temperature at which the martensite phase transforms to the austenite phase is well below human body temperature so that austenite is the only stable phase at body temperature. The excess nickel and additional alloying elements also help to provide an expanded strain range at very high stresses when the stress induced transformation of the austenite phase to the martensite phase occurs.

A presently preferred method for making the final configuration of the superelastic portions of the guiding member is to cold work, preferably by drawing, a rod or tubular member having a composition according to the relative proportions described above and then heat treating the cold worked product while it is under stress to impart a shape memory thereto. Typical initial transverse dimensions of the rod or the tubular member are about 0.045 inch and about 0.25 inch respectively. If the final product is to be tubular, a small diameter ingot, e.g. 0.25 to about 1.5 inch in diameter and 5 to about 30 inches in length, may be formed into a hollow tube by extruding or by machining a longitudinal center hole therethrough and grinding the outer surface thereof smooth. Before drawing the solid rod or tubular member, it is preferably annealed at a temperature of about 500° to about 750° C., typically about 650° C., for about 30 minutes in a protective atmosphere such as argon to relieve essentially all internal stresses. In this manner all of the specimens start the subsequent thermomechanical processing in essentially the same metallurgical condition so that products with consistent final properties are obtained. Such treatment also provides the requisite more ductility for effective cold working.

The stressed relieved stock is cold worked by drawing to effect a reduction in the cross sectional area thereof of about 30 to about 70%. The metal is drawn through one or more dies of appropriate inner diameter with a reduction per pass of about 10 to 50%. Other forms of cold working can be employed such as swaging Following cold work, the drawn wire or hollow tubular product is heat treated at a temperature between about 350° and about 600° C. for about 0.5 to about 60 minutes. Preferably, the drawn wire or hollow tubular product is simultaneously subjected to a longitudinal stress between about 5% and about 50%, preferably about 10% to about 30% of the tensile strength of the material (as measured at room temperature) in order to impart a straight "memory" to the metal and to ensure that any residual stresses therein are uniform. This memory imparting heat treatment also fixes the austenite-martensite transformation temperature for the cold worked metal. By developing a straight "memory" and maintaining uniform residual stresses in the superelastic material, there is little or no tendency for a guidewire made of this material to whip when it is torqued within a patient's blood vessel.

An alternate method for imparting a straight memory to the cold worked material includes mechanically straightening the wire or tube and then subjecting the straightened wire to a memory imparting heat treatment at a temperature of about 300° to about 450° C., preferably about 330° to about 400° C. The latter treatment provides substantially improved tensile properties, but it is not very effective on materials which have been cold worked above 55%, particularly above 60%. Materials produced in this manner exhibit stress-induced austenite to martensite phase transformation at very high levels of stress but the stress during the phase transformation is not nearly as constant as the previously discussed method. Conventional mechanical straightening means can be used such as subjecting the material to sufficient longitudinal stress to straighten it.

Figure 2:
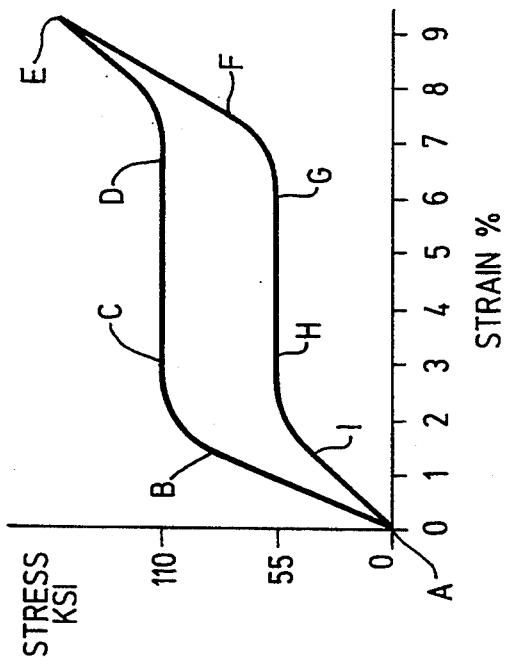
FIG. 2 is a schematic, graphical illustration of the stress-strain relationship of superelastic material.

FIG. 2 illustrates an idealized stress-strain relationship of an alloy specimen having superelastic properties as would be exhibited upon tensile testing of the specimen. The line from point A to point B thereon represents the elastic deformation of the specimen. After point B the strain or deformation is no longer proportional to the applied stress and it is in the region between point B and point C that the stress-induced transformation of the austenite phase to the martensite phase begins to occur. There can be an intermediate phase developed, sometimes called the rhombohedral phase, depending upon the composition of the alloy. At point C the material enters a region of relatively constant stress with significant deformation or strain. It is in this region that the transformation from austenite to martensite occurs. At point D the transformation to the martensite phase due to the application of tensile stress to the specimen is substantially complete. Beyond point D the martensite phase begins to deform, elastically at first, but, beyond point E, the deformation is plastic or permanent.

When the stress applied to the superelastic metal is removed, the metal will recover to its original shape, provided that there was no permanent deformation to the martensite phase. At point F in the recovery process, the metal begins to transform from the stress-induced, unstable martensite phase back to the more stable austenite phase. In the region from point G to point H, which is also an essentially constant stress region, the phase transformation from martensite back to austenite is essentially complete. The line from point I to the starting point A represents the elastic recovery of the metal to its original shape.

Because of the extended strain range under stress-induced phase transformation which is characteristic of the superelastic material described herein, a guidewire having a distal portion made at least in substantial part of such material can be readily advanced through tortuous arterial passageways. When the distal end of the guidewire engages the wall of a body lumen such as a blood vessel, it will superelastically deform as the austenite transforms to martensite. Upon the disengagement of the distal end of the guidewire from the vessel wall, the stress is reduced or eliminated from within the superelastic portion of the guidewire and it recovers to its original shape, i.e. the shape "remembered" which is preferably straight. The straight "memory" in conjunction with little or no nonuniform residual longitudinal stresses within the guidewire prevent whipping of the guidewire when it is torqued from the proximal end thereof. Moreover, due to the very high level of stress needed to transform the austenite phase to the martensite phase, there is little chance for permanent deformation of the guidewire or the guiding member when it is advanced through a patient's artery.

The tubular connector formed of superelastic alloy material provides a smooth transition between the high strength proximal portion and the relatively short distal section and retains a torque transmitting relationship between these two portions.

The present invention provides guidewires which have superelastic characteristics to facilitate the advancing thereof in a body lumen. The guiding members exhibit extensive, recoverable strain resulting from stress induced phase transformation of austenite to martensite at exceptionally high stress levels which greatly minimizes the risk of damage to arteries during the advancement therein.

The Nitinol hypotubing from which the connector is formed generally may have an outer diameter from about 0.006 inch to about 0.02 inch with wall thicknesses of about 0.001 to about 0.004 inch. A presently preferred superelastic hypotubing for the connecting member has an outer diameter of about 0.014 inch and a wall thickness of about 0.002 inch.

Superelastic NiTi alloys, such as those described herein, are very difficult to solder due to the formation of a tenacious, naturally occurring oxide coating which prevents the molten solder from wetting the surface of the alloy in a manner necessary to develop a sound, essentially oxide free, soldered joint. It has been found that by first treating the surface of the refractory superelastic alloy with molten alkali metal hydroxide, e.g. sodium, potassium, lithium or mixtures thereof to form a nascent alloy surface and then pretinning with a suitable solder such as a gold-tin solder without contacting air, that the superelastic piece can be readily soldered in a conventional manner. A presently preferred alkali metal hydroxide is a mixture of about 59% K and about 41% Na. The solder may contain from about 60 to about 85% gold and the balance tin, with the presently preferred solder containing about 80% gold and about 20% tin In a presently preferred procedure a multilayered bath is provided with an upper layer of molten alkali metal hydroxide and a lower layer of molten gold-tin solder. The part of the superelastic distal portion, which is to be soldered, is thrust into the multilayered bath through the upper surface of the molten alkali metal hydroxide which removes the oxide coating, leaving a nascent metal alloy surface, and then into the molten solder which wets the nascent metal surface. When the solder solidifies upon removal from the molten solder into a thin coating on the metal alloy surface, the underlying alloy surface is protected from an oxygen-containing atmosphere. Any of the alkali metal hydroxide on the surface of the solder can be easily removed with water without detrimentally affecting either the pretinned layer or the underlying alloy surface. The superelastic member is then ready for conventional soldering. The procedure may be employed to prepare other metal alloys having significant titanium levels for soldering.

The high strength proximal portion of the guidewire generally is significantly stronger, i.e. higher ultimate tensile strength, than the superelastic distal portion. Suitable high strength materials include 304 stainless steel which is a conventional material in guidewire construction.

While the above description of the invention is directed to presently preferred embodiments, various modifications and improvements can be made to the invention without departing therefrom.

What is claimed is:

1. An intravascular guidewire having proximal and distal ends, comprising:
    a) an elongated high strength proximal portion having proximal and distal ends;
    b) a distal portion having proximal and distal ends formed of a superelastic alloy in an austenite phase at body temperature, which transforms to a martensite phase when subjected to stress; and
    c) means for connecting the distal end of the proximal portion and the proximal end of the distal portion, which is formed at least in part of a superelastic alloy in an austenite phase which transforms to a martensite phase when subjected to stress.

2. The guidewire of claim 1 wherein the means for connecting the distal end of the proximal portion to the proximal end of the distal portion has a tubular construction with an inner lumen extending therein, with a proximal end receiving the distal end of the proximal portion and a distal end receiving the proximal end of the distal portion.

3. The guidewire of claim 2 wherein the connector means having a tubular construction has an outer diameter of about 0.006 to about 0.05 inch and a wall thickness of about 0.001 to about 0.004 inch.

4. The guidewire of claim 1 wherein a flexible coil is disposed about the distal portion and extends to a rounded plug in the distal end of the guidewire.

5. The guidewire of claim 1 wherein the distal portion terminates short of the distal end of the guidewire and a non-superelastic shaping ribbon extends from the distal section to the rounded plug.

6. The guidewire of claim 5 wherein the distal portion is formed of a superelastic alloy consisting essentially of about 40 to about 49% titanium and the balance nickel and up to 10% of other alloying elements.

7. The guidewire of claim 6 wherein the other alloying elements are selected from the group consisting of iron, cobalt, vanadium and copper.

8. The guidewire of claim 7 wherein the alloy contains vanadium or copper in amounts up to about 10% and the other alloying elements up to about 3%.

9. The guidewire of claim 1 wherein the superelastic distal portion has a straight memory.

10. The guidewire of claim 1 wherein the strain of the distal portion during the transformation from the austenite phase to the martensite phase is within the range of about 2% to about 8%.

11. The guidewire of claim 10 wherein the austenite-to-martensite transformation occurs at a relatively constant yield stress above about 50 ksi.

12. The guidewire of claim 10 wherein the austenite-to-martensite transformation occurs at a relatively constant yield stress above about 70 ksi.

13. The guidewire of claim 10 wherein the austenite-to-martensite transformation occurs at a relatively constant yield stress above about 90 ksi.

14. The guidewire of claim 1 wherein the distal portion has a section which tapers in the distal direction.

15. The guidewire of claim 1 wherein a lubricous polymer coating covers at least part of the proximal portion.

16. The guidewire of claim 1 wherein the superelastic distal portion exhibits a strain of at least 5% during the stress induced transformation from the austenite phase to the martensite phase.

17. An intravascular guidewire having proximal and distal ends, comprising:
    a) an elongated high strength proximal portion having proximal and distal ends;

b) a distal portion having proximal and distal ends formed of a superelastic alloy in a stable austenite phase at body temperature, which transforms to a martensite phase when subjected to stress; and c) a connecting member fixed to the distal end of the proximal portion and to the proximal end of the distal portion to effect a torque transmitting relationship therebetween.

18. The guidewire of claim 17 wherein a flexible coil is disposed about the distal portion and extends to a rounded plug in the distal end of the guidewire.

19. The guidewire of claim 17 wherein the superelastic distal portion has a straight memory.

20. The guidewire of claim 17 wherein the strain of the distal portion during the transformation from the austenite phase to the martensite phase is within the range of about 2% to about 8%.

21. The guidewire of claim 20 wherein the austenite-to-martensite transformation occurs at a relatively constant yield stress above about 50 ksi.

22. The guidewire of claim 20 wherein the austenite-to-martensite transformation occurs at a relatively constant yield stress above about 70 ksi.

23. The guidewire of claim 17 wherein the connector is a tubular member with an inner lumen extending therein which is configured to receive the proximal end of the distal portion and the distal end of the proximal portion.

24. The guidewire of claim 23 wherein the connector has an outer diameter of about 0.006 to about 0.05 inch and a wall thickness of about 0.001 to about 0.004 inch.

* * * * *